US005789603A

United States Patent [19]

Koehler et al.

[11] Patent Number: 5,789,603
[45] Date of Patent: Aug. 4, 1998

[54] METHOD FOR PREPARING 2-ACETYL-γ-BUTYROLACTONE

[75] Inventors: Guenther Koehler; Wilfried Uhlenbrock, both of Marl, Germany

[73] Assignee: Huels Aktiengesellschaft, Marl, Germany

[21] Appl. No.: 804,543

[22] Filed: Feb. 24, 1997

[30] Foreign Application Priority Data

Feb. 24, 1996 [DE] Germany .................. 196 06 975.0

[51] Int. Cl.$^6$ ............................. C07D 307/58
[52] U.S. Cl. ................................ 549/322
[58] Field of Search ................................ 549/322

[56] References Cited

FOREIGN PATENT DOCUMENTS 801276 12/1950 Germany .

*Primary Examiner*—Bernard Dentz
*Attorney, Agent, or Firm*—Oblon, Spivak, McClelland, Maier & Neustadt, P.C.

[57] ABSTRACT

A method is provided for the preparation of 2-acetyl-γ-butyrolactone by condensing γ-butyrolactone with an acetic acid ester in the presence of a strongly basic condensation agent, followed by protonation of the initially formed enolate, wherein the γ-butyrolactone, the acetic acid ester and the condensation agent are fed continuously into the reaction zone in a ratio of from 1.0 to 6.0 parts by mols of acetic acid ester and from 0.9 to 1.6 parts by mols of the strongly basic substance per part by mols of γ-butyrolactone, and wherein the reaction mixture formed by condensation is withdrawn from the reaction zone, either batchwise or continuously, and protonated.

18 Claims, No Drawings

METHOD FOR PREPARING 2-ACETYL-γ-BUTYROLACTONE

BACKGROUND OF THE INVENTION

1. Field of the Invention

The present invention relates to a method for preparing 2-acetyl-γ-butyrolactone by continuous reaction of γ-butyrolactone and an acetic acid ester in a condensation reaction in the presence of a strongly basic condensation agent.

2. Discussion of the Background

2-Acetyl-γ-butyrolactone is a valuable intermediate for the preparation of active ingredients for drugs, pesticides and various heterocyclic compounds.

The conventional preparation of 2-acetyl-γ-butyrolactone by condensation reaction of butyrolactone with acetic acid esters, followed by protonation (or neutralization) of the initially produced enolate is known and is represented by the following general reaction:

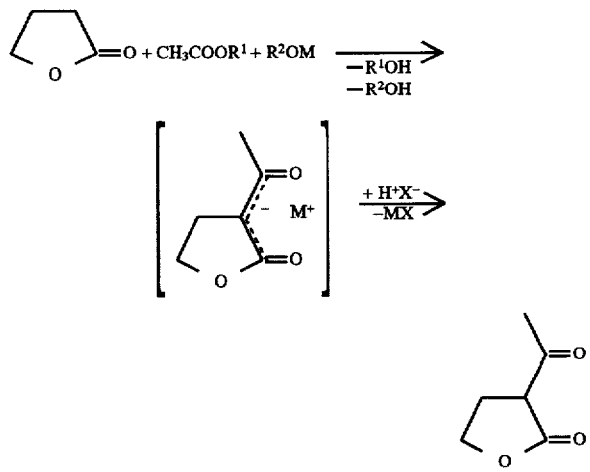

In the formulae $R^1$ and $R^2$ are identical or different lower alkyl radicals, M is an alkali metal ion or a quaternary ammonium ion, and X represents a radical of an acid and X an anion of the acid.

Acetylation of γ-butyrolactone with acetic acid esters in the presence of strongly basic substances (such as sodium, potassium, sodium amide, sodium hydride or alkali metal alcoholates) has been described by F. Korte in Angewandte Chemie, 71, 23, 709–752 (1959). According to laid-open Japanese patent application 45/009 538, butyl acetate is used specifically as the acetic acid ester and sodium butoxide as the alkali metal alcoholate.

In contrast, M. A. Lipkin et al., Khim.-Farm. Zh., 22(12) 1465–1469, recommend ethyl acetate and sodium methoxide for their batchwise method and report yields of 75% of the theoretical yields. According to laid-open Japanese patent application 58,099,473, the yield resulting from the use of these substances can be improved to 80–85% of the theoretical yield by also employing additional, highly polar solvents such as dimethylformamide and/or dimethylacetamide. In other publications, such as Polish patent 157,263 or laid-open Japanese patent application 58/162,585, acyl halides, rather than acetic acid esters, are recommended as acylation agents. In these cases, however, the yields are low and chlorinated organic by-products are formed, which can be removed by distillation but only with considerable difficulty. Moreover, the costs for the materials used are higher than with the methods employing the inexpensive acetic acid esters.

SUMMARY OF THE PRESENT INVENTION

Accordingly, one object of the present invention is to provide a process for the preparation of 2-acetyl-γ-butyrolactone that provides high purity product in a high yield and requires only a single distillation for purification of the product.

A further object of the present invention is to provide a process for the preparation of 2-acetyl-γ-butyrolactone that provides minimized side reactions and improved reaction selectivity with respect to γ-butyrolactone.

A further object of the present invention is to provide a process for the production of 2-acetyl-γ-butyrolactone that requires significantly less energy to perform and is simpler to control than conventional methods.

These and other objects of the present invention have been satisfied by the discovery of a process for the preparation of 2-acetyl-γ-butyrolactone by continuous reaction of γ-butyrolactone and an acetic acid ester in the presence of a strongly basic condensation agent, followed by protonation of the initially formed enolate, wherein the γ-butyrolactone, the acetic acid ester and the strongly basic substance, in a ratio of from 1.0 to 6.0 parts by mols of acetic acid ester and from 0.9 to 1.6 parts by mols of the strongly basic condensation agent per part by mols of γ-butyrolactone, are fed continuously into a reaction zone in which the condensation reaction takes place and from which the reaction mixture is drawn off, batchwise or continuously, and is protonated.

DETAILED DESCRIPTION OF THE PREFERRED EMBODIMENTS

The present invention relates to a method for the preparation of 2-acetyl-γ-butyrolactone from γ-butyrolactone and an acetic acid ester by reacting these two compounds in the presence of a strongly basic condensation agent, followed by protonation of the initially formed enolate, wherein the reactants are fed continuously into a reaction zone in which the condensation reaction takes place and from which the reaction mixture is drawn off, either batchwise or continuously. The reactants are used in a ratio of from 1.0 to 6.0 parts by mols of acetic acid ester and from 0.9 to 1.6 parts by mols of the strongly basic condensation agent per part by mols of γ-butyrolactone. After the reaction mixture is withdrawn from the reaction zone, it is protonated to provide the final product.

The method according to the present invention provides a number of surprising advantages. The 2-acetyl-γ-butyrolactone is obtained, after a single distillation, in >99% purity and in excellent yields of more than 90%, based on γ-butyrolactone used. Thus, the γ-butyrolactone is reacted with a high degree of selectivity. Side reactions and/or secondary reactions, which reduce the selectivity and the yield of 2-acetyl-γ-butyrolactone, are largely suppressed. Thus hydroxy- or alkoxybutyric acid derivatives, for example, which not only reduce the yield but cannot easily be separated by distillation from 2-acetyl-γ-butyrolactone, are produced in considerably smaller amounts than with the prior art methods.

The selectivity and the yield are, surprisingly, even better than they are with concomitant use of additional polar solvents according to the abovementioned laid-open Japanese patent application 58/099,473. The use of an additional polar solvent also brings a disadvantage in a reduced space-time yield and in additional distillation effort needed. This is especially true if alkali metal alcoholates are used as the strongly basic condensation agent, since during reaction they will produce additional alcohol. The concomitant use of nonpolar, inert solvents such as toluene, on the other hand, is possible without significantly impairing the yield obtained.

The present method consumes less energy and is simpler to control than the batchwise prior art methods. The present inventors have found that batchwise mixing of γ-butyrolactone with an alcoholate releases a considerable amount of heat. When sodium methoxide was used as the strongly basic condensation agent, the amount of heat generated was measured at −55 kJ per mol of γ-butyrolactone. An attempt to perform this batchwise process on an industrial scale would be too demanding in terms of control and safety, due to the switch from cooling, required at the outset, to heating, required subsequently. Further, a great deal of energy would be wasted in the switch from cooling to heating. The present method fully uses the abovementioned heat released and can be managed, in a steady state, simply and reliably in terms of control and safety, since the system does not give off any heat, and only minor readjustment is required.

Finally, the yield of 2-acetyl-γ-butyrolactone is further improved if, during the protonation step using an acid, a temperature of from −5° to +50° C. (preferably at 10° C. to 30° C.) and, in particular, a specific pH, viz. from 4 to 7 (preferably 5 to 6.5) are maintained. If the reaction mixture is introduced into the acid, or the acid is added to the reaction mixture without any special precautions, the strongly acidic environment to which the 2-acetyl-γ-butyrolactone is exposed, prior to the point of neutrality being reached, results in hydrolysis reactions with concomitant considerable losses in yield.

Suitable acetic acid esters for use in the present method include acetic acid esters with monohydric alcohols, such as methanol, ethanol, 1- and 2-propanol, 1- and 2-butanol, 2-methyl-1-propanol, 1-hexanol, 2-ethyl-1-hexanol, benzyl alcohol and β-phenylethylalcohol.

Low boiling point alcohols are preferred since their removal is easier during distillation.

Esters from alkanols having from 1 to 4 carbon atoms are more preferred with particular preference given to methyl acetate. Since the alcohol radical of the acetic acid ester is eliminated as alcohol in the course of the condensation reaction, a mixture of acetic acid esters can be used with little or no effect on the resulting product.

Any conventional strongly basic condensation agent can be used in the present invention.

Among the strongly basic condensation agents (hereafter "condensation agent"), the alkali metal alcoholates are preferred, with the lithium, sodium and potassium alcoholates being most preferred. These metal alcoholates are preferably derived from alkanols having from 1 to 4 carbon atoms. Particular preference is given to sodium ethoxide and, in particular, sodium methoxide. Other suitable condensation agents are the alkali metals, alkali metal hydrides and amides. Instead of a single condensation agent, it is also possible to use a mixture of two or more condensation agents. The condensation agent may be fed in a finely disperse form, e.g. as commercially available sodium methoxide powder, by means of conventional feeders such as proportioning screws etc. Alternatively, the finely disperse, condensation agent can be suspended in an aliquot of the acetic acid ester or in an inert nonpolar organic solvent, such as toluene. Stirred suspensions with a solids content of from 30 to 60 wt. % can often be proportioned more readily and more accurately than the solids on their own.

Preferably, the γ-butyrolactone, the acetic acid ester and the condensation agent are used in amounts of from 1.0 to 5.0, preferably from 1.05 to 2.5 parts by mols of acetic acid ester and from 1.0 to 1.5, preferably from 1.05 to 1.4 parts by mols of the condensation agent per part by mols of γ-butyrolactone. The proportion of acetic acid ester can be increased beyond the stated amounts, although the space-time yield is reduced as a result. Better reaction selectivity is achieved by feeding the reactants into the reaction zone in molar ratios within the stated limits and by keeping the molar ratios as constant as possible.

The reaction zone may be the interior of a stirred reactor or a sequence of connected reactors. In general, the reaction parameters; such as (1) amounts of substance, (2) reaction temperature and (3) mean residence time; can be matched to one another in such a way that the reaction proceeds isothermally and, at the same time, adiabatically. A reactor with heating equipment (for long mean residence times and/or small amounts of substance) and cooling equipment (for short mean residence times and/or large amounts of substance) is preferable, since it ensures the desired flexibility in controlling the reaction. However, while the reaction can have both cooling and heating capabilities, it is not necessary to switch back and forth from one to the other, since the present process runs stably and continuously.

To minimize back-mixing of the 2-acetyl-γ-butyrolactone, initially present as the alkali metal enolate, with the starting materials, the reaction zone can be subdivided by conducting the process in a reactor cascade. It is then possible to set different (generally increasing) temperatures in the various reactors. The present method can also be implemented in a flow tube where laminar flow virtually rules out any back-mixing. Here, too, a temperature gradient can be set if desired.

The optimum temperature and the optimum mean residence time in the reaction zone are interdependent. Preferably, the temperature is in the range of from 20° to 160° C., more preferably from 30° to 140° C. The mean residence time is preferably from 5 minutes to 30 hours, more preferably from 10 minutes to 20 hours. For a given acetic acid ester, a given condensation agent and a specific geometry of the reaction zone, the optimum parameters can readily be determined by preliminary trials.

The reaction mixture which leaves the reaction zone, containing 2-acetyl-γ-butyrolactone in the form of its enolate, generally has a sufficiently low viscosity at about 50° C. to be conveyable by mechanical pumps. In the case of lower temperatures and/or an only slight excess of acetic acid ester, an inert solvent such as toluene can be added to make the reaction mixture pumpable. The reaction mixture can be drawn off batchwise or, preferably, continuously from the reaction zone.

The reaction mixture is then protonated with an inorganic acid, an organic acid or an organic acid anhydride. Suitable inorganic acids include hydrohalic acids (such as hydrochloric acid), sulfuric acid, phosphoric acid, nitric acid and carbonic acid (as carbon dioxide). Suitable organic acids include carboxylic acids such as formic acid, acetic acid and propionic acid, and aliphatic or aromatic sulfonic acids such as benzene- or p-toluenesulfonic acid.

A suitable organic acid anhydride is, for example, acetic anhydride. A particularly preferred acid is sulfuric acid. The acids are preferably used with a certain percentage of water, e.g. from about 10 to 70 wt. %, so that complete protonation, without excess acid, is achieved and monitored by pH measurement. If carbonic acid or organic acid anhydride is used as the protonating agent, an appropriate amount of water should be supplied in some other way.

The protonation is preferably carried out by metering both the acid and the reaction mixture simultaneously into a protonation zone (or neutralization zone). In the process, a uniform pH is established virtually immediately in the mixture formed. The pH can, by means of conventional instrumentation and control engineering, preferably with the aid of the acid infeed as a controlled variable, be kept constant in a range which is preferably from 4 to 7, more preferably from 5 to 6.5. In the course of the protonation (or neutralization), heat is released, so that it is necessary to maintain the temperatures of the reaction mixture in the range of from −5° to +50° C., preferably from 10° to 30° C., by cooling.

To start up the plant or apparatus, acetic acid ester or an inert solvent is preferably introduced as an initial charge, after which acetic acid ester and γ-butyrolactone, separately or mixed together, and the condensation agent, as a powder or as a suspension, are fed in in the correct proportions. After some time, removal of the reaction mixture is started while, at the same time, the reactants continue to be added in the desired proportions. The amounts fed in and drawn off are controlled to ensure that the level of the liquid phase in the reactor or reactors is maintained.

Having generally described this invention, a further understanding can be obtained by reference to certain specific examples which are provided herein for purposes of illustration only and are not intended to be limiting unless otherwise specified.

EXAMPLES

Example 1

Into a 2 l glass reactor equipped with a solids feeder, 500 ml of ethyl acetate were introduced as an initial charge and heated to 55° C. Then, over a period of 60 minutes, 259 g of sodium methoxide powder were metered in via the solids feeder and, at the same time, a mixture of 344 g of γ-butyrolactone and 529 g of ethyl acetate was metered in using a metering pump. The reactor contents were kept at 55° C. by slight heating and were thoroughly mixed with the aid of a propeller mixer. The reaction mixture began to be drawn off at a rate of 1132 g/h using a further metering pump, while at the same time the infeed of 259 g/h of sodium methoxide powder and of 344 g/h of γ-butyrolactone and of 529 g/h of ethyl acetate (the latter in a mixture) continued in order to keep the liquid level in the reactor constant. The mean residence time in the reactor was about 60 minutes. After a few hours of this continuous mode a steady state was established. The conversion of the γ-butyrolactone was approximately 85%, according to GC analysis, and the selectivity of the formation of 2-acetyl-γ-butyrolactone was approximately 80%, based on γ-butyrolactone used.

The reaction mixture (1132 g/h) drawn off from the glass reactor was conveyed into a pressure-proof heatable flow tube as a second reactor, within which a temperature of 90° C. is maintained by heating. Due to the vapor pressure of the low-boiling components of the reaction mixture, an internal pressure of approximately 0.6 Mpa was established in the process. The mean residence time of the mixture in the pressure reactor was approximately 2 hours. An amount of the mixture corresponding to the reaction mixture fed in hourly was drawn off hourly as offtake.

The mixture drawn off from the pressure reactor (1132 g/h) and 296 g of 80% strength sulfuric acid were metered into a protonation reactor (or neutralization reactor) equipped with a propeller mixer, to establish a pH value of 6±0.2. The amount of the mixture in the protonation reactor was controlled in such a way that the mean residence time was approximately 4 hours. About 1430 g of protonation mixture were drawn off hourly, and sodium sulfate was suspended therein. This was removed by filtration and washed with a small amount of methanol. The filtrate was combined with the wash liquid and distilled, with the low-boiling components first being removed in a rotary evaporator. Distillation over a 20 cm column packed with Raschig rings gave 466 g/h of γ-acetylbutyrolactone which, according to GC analysis, had a purity of >99%. The yield was 91% of the theoretical yield, based on γ-butyrolactone used.

Example 2

Into a 2 l glass reactor equipped with a solids feeder and an agitator, 500 ml of methyl acetate were introduced as an initial charge and heated to 45° C. Then, over a period of 1 hour, 194 g of sodium methoxide powder were metered in via the solids feeder and, at the same time, a previously prepared mixture of 258 g of γ-butyrolactone and 422 g of methyl acetate was metered in by means of a metering pump. Initially, the reactor contents were kept at 45° C. by cooling. After about an hour, removal of the reaction mixture began, at a rate of 874 g/h, with the aid of a further metering pump, while at the same time the infeed of 194 g/h of sodium methoxide powder, 258 g/h of γ-butyrolactone and 422 g/h of methyl acetate (the latter two being mixed) continued in order to maintain a constant liquid level in the reactor and give a residence time of about 1 h. After the removal of the reaction mixture had begun, the temperature of the reactor contents was kept at 45° C. by slight heating.

With the aid of the abovementioned second metering pump, the reaction mixture drawn from the reactor was conveyed continuously to a second steel pressure reactor which had a volume of 4 l and was equipped with a propeller mixer. This steel pressure reactor was heated to an internal temperature of 100° C., and an internal pressure of 0.6 Mpa was established. This reactor was fed hourly with 874 g of reaction mixture, and the same amount of reaction mixture was drawn off.

The reaction mixture drawn off was protonated as described in Example 1, with the appropriate quantities of sulfuric acid. After removal of the sodium sulfate by filtration and washing with methanol, the filtrate and wash methanol were combined and distilled. Advantageously, the low-boiling components were first removed with the aid of a rotary evaporator or a thin-film evaporator. Distillation of the residue over a 20 cm column packed with Raschig rings gave 332 g/h of 2-acetyl-γ-butyrolactone (99% purity according to GC), which corresponds to a yield of 86% of the theoretical yield, based on γ-butyrolactone used.

Example 3

Into the 2 l glass reactor of the previous examples, 500 ml of toluene were introduced as initial charge and heated to 60° C. Over a period of 60 min, a mixture of 258 g of γ-butyrolactone and 502 g of ethyl acetate was then fed in via the metering pump, and a suspension of 244 g of sodium methoxide powder in 200 g of toluene was fed in via a laboratory gear pump. The suspension of sodium methoxide powder in toluene was thoroughly mixed in a separate receiver. Initially, the reactor was cooled, to maintain an internal temperature of the reactor of 60° C. After 1 h removal of the reaction mixture began, while the infeed of 258 g/h of γ-butyrolactone mixed with 502 g of ethyl acetate and of 244 g/h of sodium methoxide powder suspended in 200 g/h of toluene was continued. The mean residence time was approximately 1 h. The mixture drawn from the reactor was transferred into the second steel pressure cylinder described in Example 2, whose internal temperature was again 100° C., and the internal pressure was again 0.6 MPa.

The reaction mixture (1204 g/h) leaving the steel pressure cylinder was protonated in the manner described in Example 1. The sodium sulfate was filtered off and washed with methanol, the low-boiling components are first removed in a rotary evaporator, and by distillation of the residue over the 20 cm column packed with Raschig rings, 338 g of 2-acetyl-γ-butyrolactone (99% purity according to GC), corresponding to a yield of 88% of the theoretical yield, based on γ-butyrolactone used, were obtained.

Example 4

The same procedure was followed as in Example 1, except that the protonation was carried out with 50% strength phosphoric acid. Distillation gave 464 g/h of 2-acetyl-γ-butyrolactone (98.5% purity according to GC), corresponding to a yield of 91% of the theoretical yield, based on γ-butyrolactone used.

Example 5

The same procedure was followed as in Example 1, except that the protonation was carried out with 60% strength acetic acid. Distillation gave 458 g/h of 2-acetyl-γ-butyrolactone (98.5% purity according to GC), corresponding to a yield of 88% of the theoretical yield, based on γ-butyrolactone used.

This application is based on German Patent Application 196 06 975.0, filed with the German Patent Office on Feb. 24, 1996, the entire contents of which are hereby incorporated by reference.

Obviously, additional modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A method for preparing 2-acetyl-γ-butyrolactone, comprising:
   continuously feeding γ-butyrolactone, an acetic acid ester and a condensation agent to a reaction zone in a ratio of from 1.0 to 6.0 parts by mols of acetic acid ester and from 0.9 to 1.6 parts by mols of the condensation agent per part by mols of γ-butyrolactone;
   condensing γ-butyrolactone with the acetic acid ester in the reaction zone in the presence of the condensation agent to form a reaction mixture comprising a 2-acetyl-γ-butyrolactone enolate;
   withdrawing the reaction mixture from the reaction zone; and
   protonating the 2-acetyl-γ-butyrolactone enolate.

2. The method as claimed in claim 1, wherein said withdrawing step is performed batchwise.

3. The method as claimed in claim 1, wherein said withdrawing step is performed continuously.

4. The method as claimed in claim 1, wherein the condensing step is performed at a temperature in the reaction zone of from 20° to 160° C.

5. The method as claimed in claim 4, wherein the temperature in the reaction zone is from 30° to 140° C.

6. The method as claimed in claim 1, wherein the condensing step is performed with a mean residence time in the reaction zone of from 5 minutes to 30 hours.

7. The method as claimed in claim 6, wherein the mean residence time in the reaction zone is from 10 minutes to 20 hours.

8. The method as claimed in claim 1, wherein the condensing step is performed in a reactor cascade having a plurality of reactor zones.

9. The method as claimed in claim 1, wherein the acetic acid ester is an ester prepared by condensation of acetic acid with an alkanol having from 1 to 4 carbon atoms.

10. The method as claimed in claim 1, wherein the acetic acid ester is methyl acetate.

11. The method as claimed in claim 1, wherein the condensation agent is an alkali metal alcoholate of an alkanol having from 1 to 4 carbon atoms.

12. The method as claimed in claim 1, wherein the condensation agent is sodium methoxide.

13. The method as claimed in claim 11, wherein the condensation agent is fed into the reaction zone in a finely disperse form.

14. The method as claimed in claim 13, wherein the condensation agent is fed into the reaction zone in a finely disperse form suspended in an aliquot of the acetic acid ester or an inert, nonpolar solvent.

15. The method as claimed in claim 12, wherein the condensation agent is fed into the reaction zone in a finely disperse form.

16. The method as claimed in claim 15, wherein the condensation agent is fed into the reaction zone in a finely disperse form suspended in an aliquot of the acetic acid ester or an inert, nonpolar solvent.

17. The method as claimed in claim 1, wherein the protonating step is performed continuously with an inorganic acid, an organic acid or an organic acid anhydride and at a temperature of from −5° to +50° C. and a pH of from 4 to 7.

18. The method as claimed in claim 1, wherein the protonating step is performed continuously with sulfuric acid at a temperature of from 10° to 30° C. and a pH of from 5 to 6.

* * * * *